(12) United States Patent
Andersson et al.

(10) Patent No.: US 6,183,955 B1
(45) Date of Patent: Feb. 6, 2001

(54) METHODS FOR DETERMINING THE COAT COLOR GENOTYPE OF A PIG

(75) Inventors: Leif Andersson; Maria Johansson Moller, both of Uppsala (SE); Richard Wales, Cambridge (GB); Kenneth William Siggens, Cambridge (GB); Graham Stuart Plastow, Cambridge (GB)

(73) Assignee: Dalgety PLC, London (GB)

( * ) Notice: Under 35 U.S.C. 154(b), the term of this patent shall be extended for 0 days.

(21) Appl. No.: 09/014,241

(22) Filed: Jan. 27, 1998

Related U.S. Application Data

(63) Continuation-in-part of application No. PCT/GB96/01794, filed on Jul. 24, 1996.

(30) Foreign Application Priority Data

Jul. 27, 1995 (GB) .................................................. 9515385
Dec. 12, 1995 (GB) .................................................. 9525364

(51) Int. Cl.⁷ .............................. C12Q 1/68; C12P 19/34; C07H 21/04; C07H 21/02
(52) U.S. Cl. .............................. 435/6; 435/91.2; 435/810; 536/23.1; 536/24.33
(58) Field of Search ................................ 435/6, 962, 810; 536/24.33

(56) References Cited

U.S. PATENT DOCUMENTS 5,545,533 * 8/1996 Bartke et al. ........................ 435/723

FOREIGN PATENT DOCUMENTS

WO 18651 10/1992 (WO) .
93/10136 * 5/1993 (WO) .
WO 41892 12/1996 (WO) .

OTHER PUBLICATIONS

Andersson et al., "Genetic Mapping of Quantitative Trait Loci for Growth and Fatness in Pigs", *Science*, Mar. 25, 1994, 263:1771–1774.

Bernstein et al., "The mouse W/c–kit locus", *Molecular Control if Haemopoiesis*, 1990, Ciba Foundation Symposium 148:158–172.

Besmer et al., "A new acute transforming feline retrovirus and relationship of its oncogene v–kit with the protein kinase gene family", Apr. 3, 1986, *Nature* 320:415–421.

Chabot et al., "The proto–oncogene c–kit encoding a transmembrane tyrosine kinase receptor maps to the mouse W locus", Sep. 1, 1988, *Letters to Nature* 335:88–89.

Coppieters et al., "Characterization of porcine polymorphic microsatellite loci", 1993, *Animal Genetics* 24:163–170.

De Sepulveda et al., "Instability at the W/c–kit locus in mice: analysis of melanocyte cell lines derived from reversion spots", 1994, *Oncogene* 9:2655–2661 p. 2659 missing.

Ezashi et al., "The gene for the β subunit of porcine LH: clusters of GC boxes and CACCC elements", 1990, *Journal of Molecular Endocrinology* 5:137–146.

Fleischman et al., "Deletion of the c–kit protooncogene in the human developmental defect piebald trait", Dec. 1991, *Proc. Natl. Acad. Sci., USA* 88:10885–10889.

Giebel et al., "Organization and nucleotide sequence of the human KIT (mast/stem cell growth factor receptor) proto–oncogene", 1992, *Onocgene* 7:2207–2217.

Geissler et al., "The Dominant–White Spotting (W) Locus of the Mouse Encodes the c–kit Proto–Oncogene", Oct. 7, 1988, *Cell* 55:185–192.

Gokkel et al, "Structural organization of the murine c–kit proto–oncogene", 1992, *Oncogene* 7:1423–1429.

Johansson et al., "the Gene for Dominant White color in the Pig Is Closely Linked to ALB and PDGFRA on Chromosome 8", 1992, *Genomics* 14:965–969.

Kato et al., "The gene for the common α subunit of porcine pituitary glycoprotein hormone", 1991, *Journal of Molecular Endocrinology* 7:27–34.

Nocka et al., "Molecular bases of dominant negative and loss of function mutations at the murine c–kit/white spotting locus: $W^{37}$, $W^v$, $W^{41}$, and W", 1990, *The EMBO Journal* vol. 9 No. 6:1805–1813.

Rohrer et al., "A Microsatellite Linkage Map of the Porcine Genome", Jan. 1994, *Genetics* 136:231–245.

* cited by examiner

*Primary Examiner*—Stephanie Zitomer
(74) *Attorney, Agent, or Firm*—Brobeck, Phleger & Harrison, LLP

(57) ABSTRACT

Coat color is important to the pig breeding industry for a number of reasons. It is therefore desirable to develop populations of pigs which will breed true for coat color. However, establishing such populations would be time-consuming and costly using traditional test mating programs. It is therefore desirable to determine the coat color genotype of individual pigs. The inventors have shown that the KIT gene in pigs is involved with coat color determination. Specifically, the inventors have discovered that the difference between the I, $I^P$, and i alleles of the coat color determining gene is duplication of at least part of the KIT gene in the I and $I^P$ alleles. Further, the inventors have discovered that the difference between the I and $I^P$ alleles is that, although both I and $I^P$ have a duplication in the KIT gene, only I and not $I^P$ exhibits a deletion in one of the duplicated regions. These discoveries have allowed the inventors to develop methods for distinguishing between the alleles I, $I^P$, and i, thereby determining the genotype of individual pigs with respect to coat color. In accordance with the present invention, there are provided methods for determining the genotype of individual pigs with respect to coat color and kits for use in carrying out such methods.

36 Claims, 1 Drawing Sheet

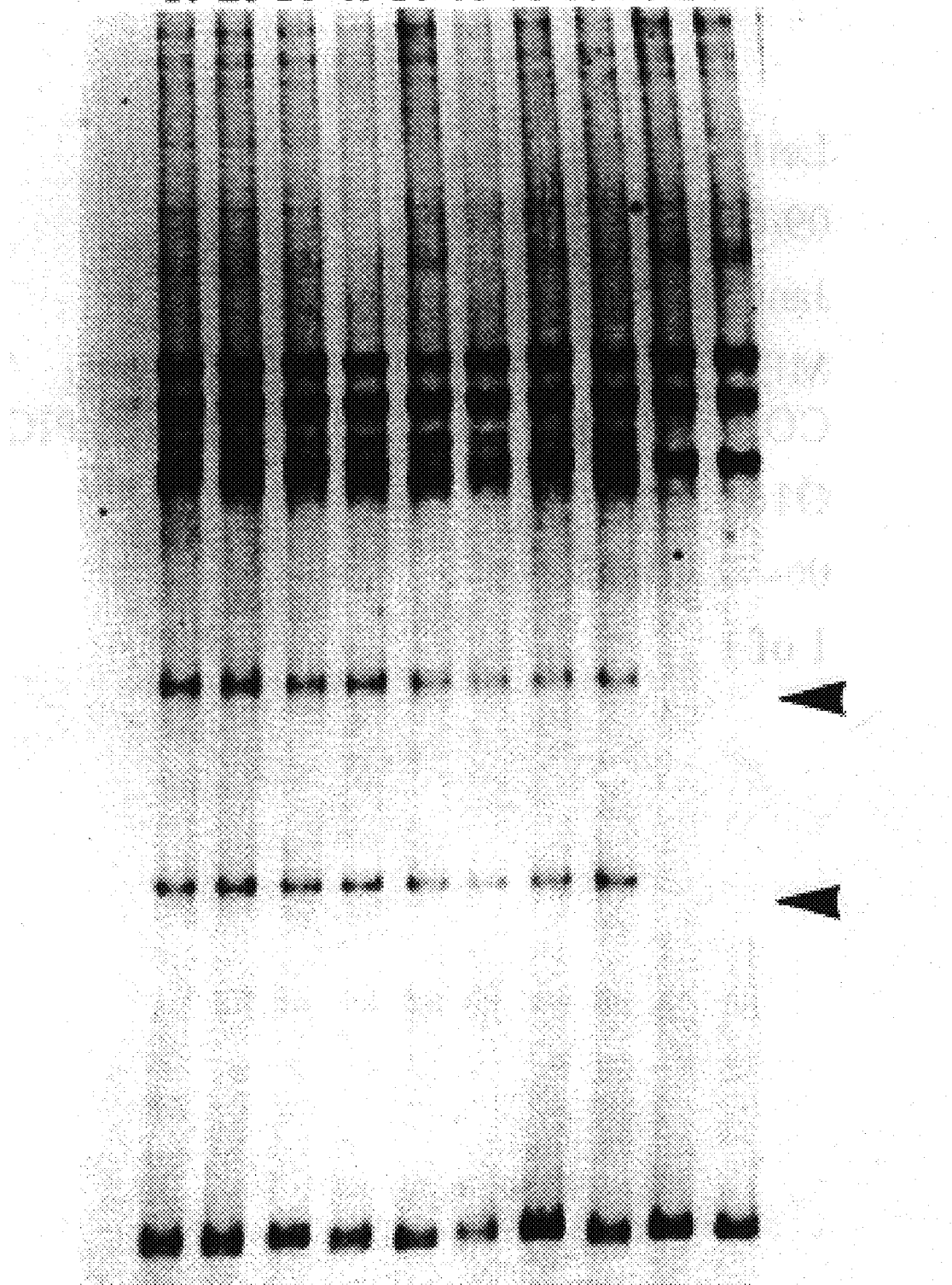

SEQUENCE LISTING

<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Derivative of pig sequence

<400> SEQUENCE: 1
gaatattgtt gctatggtga tctcc            25

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Derivative of pig sequence

<400> SEQUENCE: 2
ccgcttctgc gtgatcttcc tg            22

```
<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 3
ggyaatcaca tgaatattgt gaa                                              23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 4
tcaccatagc aacaatattc tgt                                              23

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 5
tcrtacatag aaagagaygt gactc                                            25

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 6
cctttracca crtaattmga atc                                              23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 7
gtgatgrtkc tsacctacaa ata                                              23

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 8
gtctatgtaa acataattgt ttcc                                             24
```

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 9
ctggatgtcc tgtgttccct gt                                              22

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 10
aggtttgtct gcagcagaag ctc                                             23

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 11
gatgaacttt gaggtccctg aggag                                           25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 12
tttcttctga gaatgccgaa gatctg                                          26

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 13
tgtgggagct cttctcttta gg                                              22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 14
ccagcaggac aatgggaaca tct                                             23

<210> SEQ ID NO 15

-continued

```
<211> LENGTH: 26
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 15
gaaagtgayg tctggtccta tsggat                                         26

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Derivative
      of pig sequence

<400> SEQUENCE: 16
agccttcctt gatcatcttg tag                                            23
```

METHODS FOR DETERMINING THE COAT COLOR GENOTYPE OF A PIG

This application is a continuation-in-part of International Appl. Ser. No. PCT/GB96/01794 filed Jul. 24, 1996.

The present invention relates to methods of screening pig nucleic acid to determine pig genotype with respect to coat colour, and to kits for use in carrying out such methods.

White is the predominant coat colour among European commercial pig breeds e.g. Large White and Landrace. However, there are a number of commercially important coloured breeds, demonstrating a number of colours and combinations. The Duroc, associated with meat tenderness, is red, the Pietrain, which is a heavily muscled animal which produces a very lean carcass, is spotted, and the prolific Chinese Meishan breed is black.

Coat colour is important to the pig breeding industry for a number of reasons. Firstly, in a number of markets there is a preference for white skinned meat. This is due to the fact that pork is often marketed with the skin still attached, and skins from coloured pigs, even if dehaired, can still exhibit coloured hair roots, which can lead to a negative perception by the consumer, since the surface of the meat may appear to be spotted by mould. It is necessary, therefore, in these markets, to remove the skin from such carcasses, entailing additional cost. For example, in the U.S., coloured carcasses are associated with approximately 1% of skin defects requiring dehairing and skinning to remove pigment. As a result of this, coloured pig carcasses are generally discounted.

Secondly, gross variation in the appearance (i.e. a range of coat colours) of pigs claimed to be genetically consistent for traits other than coat colour can lead to questions about the consistency and quality of the animals in the mind of pig-producing customers.

In addition, pig breeders would like to be able to be in a position to ensure consistency in breeding populations. Thus, breeders may wish to ensure that progeny produced by breeding crosses were always white. Alternatively, a breeder of Pietrain pigs may wish to ensure that breeding crosses always produced the characteristic Pietrain colouring. Traditional animal breeding practices have, in the past, been used to attempt to eliminate colour (other than white) from pig lines.

The gene determining whether the animal is coloured or the desired white is designated I (for inhibition of coat colour). The version of the gene preventing the expression of any colour (I) is dominant to that which allows colour to develop (i). Traditional selection for white animals has reduced the frequency of i, but it still remains in the population in white heterozygous carrier animals. These animals can only be identified when they produce coloured offspring through matings with other heterozygous animals. Only through a programme of test matings can heterozygotes be identified which would enable the recessive allele to be eliminated from a given population. Such a programme would be time-consuming and costly and as such is not cost effective. Thus, i/i animals will inevitably be produced.

In addition, the situation is complicated further by the existence of another allele of I called $I^P$ (I-patch). The $I^P$ allele is recessive to I but is dominant to i. Thus, animals which have the genotype $I^P/I^P$ or $I^P/i$ will show patches of colour.

Using a reference family developed from crosses between the European wild pig and a large white breed (Swedish Yorkshire), the position of the I gene on the porcine genetic map has been determined. The gene is located on chromosome 8 in the pig, close to the genes for albumin and for the α-subunit of platelet-derived growth factor (PDGFRA) (Johansson et al, *Genomics* 14: 965–969 (1992)). The mouse genetic map includes a homologous region located on mouse chromosome 5. This region contains a number of genes playing a role in the determination of mouse coat colour, namely W (dominant white spotting), Ph (patch) and Rw (rump white). The mouse W gene has been shown to co-locate with the KIT gene and some mutant genotypes at the W locus are due to structural changes in the KIT gene (Chabot et al, *Nature* 335: 88–89 (1988), Geissler et al, *Cell* 55: 185–192 (1988) and Nocka et al, *EMBO Journal* 9: 1805–1813 (1990)).

We have now found that the KIT gene in pigs is involved with coat colour determination. More particularly, we have found that the difference between I, or $I^P$, and i is duplication of at least part of the KIT gene in the I or $I^P$ allele. This duplication can result in two or more copies of a particular region of the KIT gene being present.

Thus, this has allowed us to develop methods of distinguishing between the alleles I, $I^P$ and i, and thus for determining the genotype of individual pigs with respect to coat colour.

Therefore, in a first aspect, the present invention provides a method of determining the coat colour genotype of a pig which comprises:

(i) obtaining a sample of pig nucleic acid; and
(ii) analysing the nucleic acid obtained in (i) to determine whether duplication of all or part of the KIT gene is present The presence of duplication in the KIT gene sequence indicates the presence of either the I or $I^P$ allele. In some pig populations it is known that the incidence of $I^P$ is low or indeed non-existent. In such populations determining the presence or absence of duplication will be sufficient to provide a reasonable degree of confidence concerning a particular pig's genotype. Thus, by means of simply determining the presence or absence of duplication of the KIT gene (either complete or part thereof), coat colour genotype of a particular pig can be determined with a reasonably high degree of certainty.

However, in other populations it will be necessary to distinguish between the presence of I and $I^P$.

We have found that although both I and $I^P$ have a duplication in the KIT gene, only I and not $I^P$ exhibits a deletion in one of the duplicated regions. It is therefore possible to distinguish between these alleles on that basis.

Thus, the method may further comprise the step:

(iii) determining whether the duplication is due to the presence of I or $I^P$.

Suitably, this determination is made by analysing for the presence or absence of a deletion in at least one of the duplicated regions.

Suitably, the method of the invention will be carried out on pig genomic DNA, although pig RNA may also be analysed to determine the presence or absence of duplication in the KIT gene.

There may be a number of effects on the production of RNA from this gene, resulting from the duplication of part of the DNA sequence. These could include the inhibition of the production of RNA, alteration of the level of synthesis of the RNA, alteration in the size or processing kinetics of the RNA or alteration in the distribution of RNA production throughout the body of the animal. There might also be effects on the production of RNA from other genes caused by epistatic effects of the duplication.

Preferably, the determination carried out in step (ii) involves the use of PCR techniques, using an appropriate pair of primers. PCR, or polymerase chain reaction, is a widely used procedure in which a defined region of a DNA molecule can be amplified in vitro using a thermostable version of the enzyme DNA polymerase. Two known sequences that flank the region to be amplified are selected and priming oligonucleotides synthesised to correspond to these regions. If the primers are located sufficiently close together on the same piece of DNA, the region between them will be amplified. A polymerase chain reaction consists of a number of cycles of amplification. Each cycle begins with a denaturation step, typically at 94° C., in which the two strands of the template DNA molecule are separated. The temperature is then dropped to a temperature at which the synthetic oligonucleotide primers can anneal to the template (typically 50–60° C.). Through the high concentration of primers relative to template, the primers anneal to the template before template-template hybrids form. The annealing temperature is chosen such that annealing only occurs to the complementary regions of DNA within the template, and not to other regions of imperfect complementarity. The temperature is then raised to 72° C., at which the thermostable DNA polymerase can extend the bound primer, thus producing the strand of DNA complementary to the template.

In the earlier stages of the reaction, each cycle results in two-fold amplification of the template present. As each of these newly synthesised strands can function as template, the increase in molecules corresponding to the defined region is exponential. However, in the later stages of the reaction (typically 25 cycles onwards) the amplification ceases to be exponential due to depletion of reaction constituents (e.g. primers), and the increased concentration of template molecules leading to increased template-template hybrid formation at the annealing stage. In such reactions, the amount of product is directly related to the amount of template initially present, but only in the exponential phase. It is critical in quantitative applications as described herein that the number of cycles used ensures that the reaction remains within the exponential phase.

The PCR can be used in several ways to determine whether or not duplication of the KIT gene is present. Firstly, the primers can be chosen such that amplification of a portion of the KIT gene duplicated in I or $I^P$ and not in i are used. This PCR is compared to a second PCR using primers which allow amplification of a control sequence which is known to be present in only a single copy of any chromosome. Comparison of the ratios of the individual PCR reaction products will enable an estimation of the duplication of the KIT region present, if any. Clearly, if it is assumed that the region of DNA in question is present in two copies in the I or $I^P$ and in only one copy in the i allele, then the ratios of KIT product to control product expected will be as follows:

| GENOTYPE | KIT/CONTROL |
| --- | --- |
| I/I | 2 |
| $I^P$/I | 2 |
| $I^P$/$I^P$ | 2 |
| I/i | 1.5 |
| $I^P$/i | 1.5 |
| i/i | 1 |

In practice, the ratios obtained may vary from this due to differences in the reaction kinetics of the two amplification reactions which are occurring.

Pairs of suitable primers for use with the above described method include:

GAATATTGTTGCTATGGTGATCTCC KIT1-FOR (SEQ ID NO: 1)
CCGCTTCTGCGTGATCTTCCTG KIT1-REV (SEQ ID NO: 2)
and
GG(C/T)AATCACATGAATATTGTGAA KIT2-FOR (SEQ ID NO: 3)
TCACCATAGCAACAATATTCTGT KIT2-REV (SEQ ID NO: 4)
and
TC(A/G)TACATAGAAAGAGA(C/T)GTGACTC KIT3-FOR (SEQ ID NO: 5)
CCTTT(A/G)ACCAC(A/G)TAATT(A/C)GAATC KIT3-REV (SEQ ID NO: 6)
and
GTGATG(A/G)T(G/T)CT(C/G)ACCTACAAATA KIT4-FOR (SEQ ID NO: 7)
GTCTATGTAAACATAATTGTTTCC KIT4-REV (SEQ ID NO: 8)

As described above, the inclusion of a control PCR reaction allowing direct comparison to determine the ratio of amplified product is preferred.

This is suitably achieved by reference to a control sequence chosen because it is known that the pig chromosome carries only a single copy. Thus, by employing suitable primers for that control sequence, a PCR product can be generated and quantified. Comparison with the KIT gene PCR product thus provides a direct reading of the degree of duplication.

One example of a suitable control sequence is part of an exon of the muscle calcium release channel gene (CRC) and a suitable pair of primers is:

CTGGATGTCCTGTGTTCCCTGT CRC FORWARD (SEQ ID NO:9)

AGGTTTGTCTGCAGCAGAAGCTC CRC REVERSE (SEQ ID NO:10)

Another example of a suitable control sequence is part of the porcine interferon-β gene (Artursson et al, *Journal of Interferon Research* 12: 153–160 (1992)), and a suitable set of primers is:

(SEQ ID NO:11)
GATGAACTTTGAGGTCCCTGAGGAG    IFN-b Forward (SEQ ID NO:11)
TTTCTTCTGAGAATGCCGAAGATCTG    IFN-b Reverse Other suitable sequences for control primers include regions from the gene for the common α subunit of porcine pituitary glycoprotein hormone (Kato et al, *Journal of Molecular Endocrinology* 7: 27–34 (1991)), the gene for the β subunit of porcine luteinizing hormone (Ezashi et al, *Journal of Molecular Endocrinology* 5: 137–146 (1990)) or any other single copy porcine gene.

Most preferably, the PCR for the KIT gene and that for the control sequence are carried out simultaneously on a single sample of pig DNA.

A second method for determining whether any duplication of the KIT gene (including a part thereof) is present relies on the fact that at the boundary of any duplicated region there will be present a nucleotide sequence unique to the I allele. Therefore, by utilising primers specific for such boundary nucleotide sequences, or junctions, it is possible to determine the frequency of the I allele.

A third method for the determination of the structure of the KIT gene is to use a linked genetic polymorphism which is closely associated with the presence or absence of the duplication. Such a polymorphism may occur in the KIT gene itself or in a chromosomal region linked to KIT. By using a single linked marker in complete association with the presence/absence of the duplication or a combination of markers showing a partial association a highly informative test can be developed. For instance, the SSCP (Single Strand Conformation Polymorphism) method may be used to develop such polymorphism. The principle of the method is that double-stranded DNA, produced by PCR, is denatured into single-stranded DNA which is then separated by non-denaturating gel electrophoresis. Under non-denaturating conditions the single-stranded DNA forms a secondary structure due to intrastrand interaction but a proportion of the single-stranded DNA will renature and form double-stranded DNA. Two types of polymorphism may be revealed by this method. Firstly, a difference in nucleotide sequence between two alleles may influence the secondary structure of single-stranded DNA which is revealed as a difference in the mobility rate during electrophoresis. Secondly, a difference in nucleotide sequence often influences the mobility of the heteroduplex DNA (A heteroduplex is a double-stranded DNA molecule formed by two single-stranded molecules representing different alleles).

A fourth method of determining the structure of the KIT gene in relation to the number of copies of the region subject to duplication involves the use of pulsed field gel electrophoresis. Pulsed field gel electrophoresis being a technique in which the size of large DNA fragments can be analysed. In this application the process would be to utilize a restriction endonuclease that cleaved the genomic DNA at specific sites flanking the region found to be duplicated in the DNA of animals carrying the I allele of the KIT gene. Genomic DNA cleaved with such an enzyme would be subject to pulsed field electrophoresis followed by transfer to a DNA binding membrane. A probe specific for the region subject to duplication could then be used to determine the original location on the gel, and therefore the size of that fragment by comparison to suitable DNA size standards. Should the DNA from an animal contain a duplication of a portion of the KIT gene, this specific fragment would be increased in size. Heterozygous animals will be found to show two differently sized specific bands, the smaller representing the non duplicated allele i, the larger representing the duplicated allele I or $I^P$. This technique will also show alleles containing more than two copies of the duplicated region through the presence of fragments having a further increase in size by the unit length of the duplication.

In a second aspect, the present invention provides a method for determining the coat colour genotype in pigs, which comprises:
  (i) obtaining a sample of pig genomic DNA;
  (ii) hybridising the genomic DNA from (i) with one or more suitable primers;
  (iii) carrying out one or more PCR cycles using the hybridised nucleic acid from (ii); and
  (iv) determining the amount of PCR reaction product.

The method of this aspect may also include a further step:
  (v) determining whether any duplication present is due to the presence of I or $I^P$.

Suitably, this determination is carried out by analysing for the presence or absence of a deletion in at least one of the duplicated regions.

Association between genetic markers and genes responsible for a particular trait can be disrupted by genetic recombination. Thus, the closer the physical distance between the marker and the gene in question, the less likely it is that recombination will separate them. It is also possible to establish linkage between specific alleles of alternative DNA markers and alleles of DNA markers known to be associated with a particular gene (e.g. the KIT gene discussed herein), which have previously been shown to be associated with a particular trait. Thus, in the present situation, taking the KIT gene, it would be possible, at least in the short term, to select for pigs with a particular coat colour, indirectly, by selecting for certain alleles of a KIT gene associated marker through the selection of specific alleles of alternative chromosome 8 markers. Examples of such markers known to be linked to the KIT gene on porcine chromosome 8 include genetic polymorphism in the KIT gene itself or in the closely linked genes for the α-subunit of platelet derived growth factor (PDGFRA) and albumin.

Particular genetic markers associated with the KIT gene are microsatellites. These are simple sequence repeats of 4, 3 or, more usually, 2 nucleotides, which occur essentially at random around the genome at approximately every 50,000 bases (about 60,000 microsatellites per haploid genome). Stuttering of DNA polymerase during replication and unequal crossing-over during recombination are thought to result in the loss or gain of repeat units. This means that microsatellites are usually polymorphic and can have several repeat length alleles.

Examples of linked microsatellite sequences include S0086 (Ellegren et al, *Genomics*, 16: 431–439 (1993)), S0017 (Coppieters et al, *Animal Genetics* 24: 163–170 (1993)), Sw527, Swr750 and SW916 (Rhorer et al, *Genetics*, 136: 231–245 (1994)). It would be possible to select indirectly for alleles of the KIT gene linked to coat colour using any of the above markers, or indeed any other linked markers on porcine chromosome 8.

As discussed herein, the present invention relies upon a determination of KIT gene DNA sequence copy number. To that end a nucleotide probe representing the duplicated KIT segment, or part of it or indeed any other nucleotide probe showing sufficient similarity to such a porcine probe may be used. For example, the following methods can be used to carry out such a determination:
  (i) using nucleotide probes derived from nucleotide sequences of at least part of the DNA of the KIT gene, and RNA derived from it, from, e.g. mouse (Gokkel et al, *Oncogene* 7, 1423–1429 (1992)) and/or man (Giebel et al, *Oncogene* 7, 2207–2217 (1992)). Such probes, due to conservation, would hybridise to the pig gene;
  (ii) where the amino acid sequence of the KIT protein of an animal is known, the possible nucleotide sequences of the DNA encoding that protein, or portions of it, can be deduced. Based on that, mixed oligonucleotide preparations can be used as probes for the pig KIT gene;
  (iii) probes can be designed based on the protein sequences (and corresponding nucleotide sequences) for proteins that have functional homologies to the whole or part of the KIT gene, for example v-KIT (Besmer et al, *Nature* 320: 415–421 (1986)).

All of the probes derived as described above may be used to probe animal derived nucleic acid preparations transferred to suitable matrices for hybridisation such as Nylon membranes (e.g. Hybond N Amersham International) by Southern, northern or dot blotting. The ratio of the amounts of the KIT and control probes hybridising to the matrix bound nucleic acid can be used to determine KIT copy numbers. The amount of bound probes can be quantified through labelling the probes with radioactive isotopes. Other, non-isotopic nucleic acid labelling kits are now available and can also be used.

The reverse of the procedure involving hybridisation of animal derived nucleic acid to matrix is also possible. In this, probe is bound to the matrix and used to capture, through a hybridisation protocol, genomic DNA or RNA labelled in such a way as previously described, thus allowing quantitation of the amount bound. The amount bound is, if the conditions are correct, related to the total amounts (or copy number) of the KIT and control nucleic acid sequences present.

Other methods of quantifying PCR amplified DNA include radiolabelling based methods. An example is radiolabelling of one or both of the oligonucleotide primers, followed by quantitation of the radioactivity in the PCR product through densitometry of autoradiographs of DNA gels. An alternative procedure is the differential labelling of the oligonucleotides for the two products of the PCR reaction with different isotopes allowing quantification of each separate product after removal of unincorporated labelled oligonucleotides through precipitation, filtration, differential centrifugation or other procedures. PCR product can also be quantitated using other staining procedures utilising dyes such as ethidium bromide or SYBR green (Molecular Probes, Inc.) in combination with densitometry or fluorimetry.

Yet another method of quantifying the products of a differential PCR in which two PCRs proceed in the same tube to produce two separate products, as described in this patent, is the use of the TaqMan™ system (Perkin Elmer Corp.). In this system, in addition to the two oligonucleotide primers flanking the region to be amplified a third oligonucleotide probe is used that binds to the amplified region. The flanking primers are unlabelled while the probe carries two fluorescent labels. On the 3' end of the probe is a reporter dye, the fluoresence of which is quenched by a separate fluorophore attached to the 5' end of the probe. During PCR this probe binds to the product DNA molecules. As PCR proceeds these products are used as templates during which the Taq DNA polymerase cleaves off the 5' quenching dye of the probe as it displaces it. This removal of the quenching agent allows fluoresence from the reporter dye to be detected. The degree of fluoresence is proportional to, and therefore a measure of, the amount of PCR product produced. A reaction may include two separate sets of PCR primers and two probes, each corresponding to a separate genomic DNA region. In this way, as long as the criteria for quantitative PCR are obeyed, the relative amounts of each template region can be measured.

Protein nucleic acids might be used in any of the above hybridisation procedures (PerSeptive Biosystems, Inc., Cambridge, Mass.).

In a third aspect, the invention provides a method for determining the coat colour genotype of a pig, which method comprises:

(i) obtaining a sample of pig KIT protein; and
(ii) analysing the protein obtained in (i) to determine whether duplication of all or part of the KIT gene is present.

Antibodies raised against epitopes of KIT or related proteins could be used to determine the level or form of the c-KIT proteins present in the animal through Western blotting or ELISA procedures. Also antibodies could be raised against the different DNA structures comprising the various alleles of the KIT gene and the genotype determined through ELISA techniques.

In a fourth aspect, the invention provides a kit for determining the coat colour genotype of a pig, comprising one or more reagents capable of indicating the presence of duplication of all or part of the KIT gene sequence in pig genomic DNA.

It will also be appreciated from the discussion above concerning the difference between I and $I^P$, that this difference can also be exploited to distinguish between genotypes. As the deletion only appears to be present in one of the duplicated regions of I (where I contains two copies of the duplicated region) and not in i, it provides a marker of I. Oligonucleotide primers can be designed to hybridize to genomic DNA either side of the position at which the deletion is found and PCR carried out, resulting in two possible sizes of product.

That obtained where the four base pair deletion is present will be four base pairs shorter than that from the same region where the deletion is not present. The relative amount of these two products can be determined by any of the methods previously discussed, but one preferred method involves having one of the oligonucleotide primers labelled with a fluorescent dye combined with electrophoresis in an apparatus with suitable detection equipment or the TaqMan apparatus (Perkin-Elmer).

One particular advantage of this testing strategy regarding the PCR component is that it is not so susceptible to loss of discrimination as the PCR leaves the exponential phase. The primers, their binding sites and the products are the same or similar for the non-deleted and deleted template regions, thus, the rate of production of one product relative to the other is unlikely to vary at different stages of the reaction. As the formation of template/template hybrids begins to compete with the formation of template/primer complexes it affects both sub-reactions simultaneously. The overall result is a high degree of similarity between the kinetics of the production of each product.

In a line of pigs containing only I or i and not $I^P$ the ratio of the two products obtained can be related to the genotype as shown below, based upon the fact that each copy of the I allele gives rise to equal amounts of the undeleted and deleted product while i gives only the undeleted product.

| Genotype | Copies of undeleted region present | Copies of deleted region present | Ratio of undeleted to deleted product |
|---|---|---|---|
| II | 2 | 2 | 1:1 |
| Ii | 2 | 1 | 2:1 |
| ii | 2 | 0 | 2:0 |
| II$^P$ | 3 | 1 | 3:1 |
| I$^P$I$^P$ | 4 | 0 | 4:0 |
| I$^P$i | 3 | 0 | 3:0 |

In a fifth aspect, therefore, the present invention provides a method of determining the coat colour genotype of a pig which comprises:

(i) obtaining a sample of pig nucleic acid; and (ii) analysing the nucleic acid obtained in (i) to identify the presence or absence of a deletion in the KIT gene sequence.

Simply by identifying the presence or absence of the deletion, one can distinguish between I and i. Of course the presence of $I^P$ complicates the results since, due to the absence of the deletion in one copy of the duplication $I^P$ will effectively mimic i in such a test. Thus, the use of this method on lines carrying $I^P$ may result in the misidentification of animals carrying this allele as ii. However, such a method may still find use, for instance in certain aspects of animal breeding where all that is required is the positive identification of animals which are homozygous for I.

Of course, it will also be appreciated that each individual genotype either generates a different ratio of the two products, or produces different amounts of a single product type. Thus, such a test will also provide a means of determining the absolute genotype of an individual animal by means of quantification of the product produced. In such a case the amounts of DNA used in each test should be controlled in order to ensure that differences in the amount of product can be accurately determined.

Preferably, the determination step (ii) involves PCR amplification, usually on a sample of pig genomic DNA. Suitable pairs of primers which can be used in such a PCR method include:

TGTGGGAGCTCTTCTCTTTAGG KITDEL1-FOR (SEQ ID NO: 13)

CCAGCAGGACAATGGGAACATCT KITDEL1-REV (SEQ ID NO: 14)

and

GAAAGTGA(C/T)GTCTGGTCCTAT(C/G)GGAT KITDEL2-FOR (SEQ ID NO: 15)

AGCCTTCCTTGATCATCTTGTAG KITDEL2-REV (SEQ ID NO: 16)

One of numerous alternative ways of approaching this would be to use, in PCR, primers that bind to the unique nucleotide sequences created in each version of this region of the KIT gene through the presence or absence of the deletion. Such primers could be designed such that they only yielded a product in the presence of the corresponding sequence. Hence, if each of the two alternative primers was used with a different fluorescent label, separation by gel electrophoresis would not be required, identification of each product being made on the basis of their fluorescence.

There is preliminary evidence based upon the inheritance of specific values for ratios obtained when testing for the presence of the duplication and the number of copies of the deletion that alleles of I containing more than two copies of the duplicated region exist in certain breeds of pig.

The discrimination between animals with these varying forms of I can be enhanced using a combination of the ratio arising from the determination of the number of copies of the duplicated region present with that from the determination of the presence of the deletion. The structure of the KIT gene in alleles that might be present given the existence of duplicated versions with more than two copies is shown below:

| ALLELE | COPIES OF DUPLICATED REGION | COPIES OF DUPLICATED REGION CONTAINING DELETION |
|---|---|---|
| i | 1 | 0 |
| $I^P$ (I 2.0) | 2 | 0 |
| I 2.1 | 2 | 1 |
| I 3.0 | 3 | 0 |
| I 3.1 | 3 | 1 |
| I 3.2 | 3 | 2 |

The possible genotypes arising from the presence of these alleles and the respective ratios obtained in the determinations of the assay for the number of copies of the duplicated region and that for the number of copies containing the deletion are shown below:

| GENOTYPE | RATIO: copies of KIT region/copies of control region | RATIO copies of non deleted region/ copies of deleted region |
|---|---|---|
| i/i | 1.0 | 0.0 |
| $I^P$/i | 1.5 | 0.0 |
| I2.1/I | 1.5 | 2.0 |
| I3.0/i | 2.0 | 0.0 |
| I3.1/i | 2.0 | 3.0 |
| I3.2/i | 2.0 | 1.0 |
| $I^P/I^P$ | 2.0 | 0.0 |
| I2.1/$I^P$ | 2.0 | 3.0 |
| I3.0/$I^P$ | 2.5 | 0.0 |
| I3.1/$I^P$ | 2.5 | 4.0 |
| I3.2/$I^P$ | 2.5 | 1.5 |
| I2.1/I2.1 | 2.0 | 1.0 |
| I3.0/I2.1 | 2.5 | 4.0 |
| I3.1/I2.1 | 2.5 | 1.5 |
| I3.2/I2.1 | 2.5 | 0.67 |
| I3.0/I3.0 | 3.0 | 0.0 |
| I3.1/I3.0 | 3.0 | 5.0 |
| I3.2/I3.0 | 3.0 | 2.0 |
| I3.1/I3.1 | 3.0 | 2.0 |
| I3.2/I3.1 | 3.0 | 1.0 |
| I3.2/I3.2 | 3.0 | 0.5 |

One method by which the two tests may be combined involves the use of the TaqMan™ system (Perkin Elmer Corp.). In this specific application of TaqMan three probes are used with two sets of PCR primers. One probe allows the measurement of the control product arising from one of the sets of primers, the other set of PCR primers allow the amplification of the region of the duplication that may or may not contain the deletion. The remaining probes detect either the deleted or non-deleted products from this amplification. From the data obtained two calculations can be made as below providing the values as obtained from the two separate tests described previously.

A: copies of KIT gene region: copies of control region
   (non-deleted KIT gene product+deleted KIT gene product)
   control gene product B: non deleted KIT gene: deleted KIT gene
   non-deleted KIT gene
   deleted KIT gene Where appropriate, preferred features of each aspect of the invention are applicable to each other aspect mutatis mutandis.

The invention will now be described with reference to the following examples which should not be construed as in any way limiting the invention.

Example 3 refers to FIG. 1 wherein:
FIG. 1: shows the results of SSCP analysis.

EXAMPLE 1

(i) DNA Preparation

DNA can be prepared from any source of tissue containing cell nuclei, for example white blood cells, hair follicles, ear notches and muscle. The procedure outlined here relates to blood cell preparations; other tissues can be processed similarly by directly suspending material in K buffer and then proceeding from the same stage of the blood procedure. The method outlined here produces a cell lysate containing crude DNA which is suitable for PCR amplification. However, any method for preparing purified, or crude, DNA should be equally effective.

Blood was collected in 50 mM EDTA pH 8.0 to prevent coagulation. 50 μl of blood was dispersed into a small microcentrifuge tube (0.5 ml Eppendorf or equivalent). 450 μl of TE buffer was added to lyse the red blood cells (haem groups inhibit PCR) and the mix vortexed for 2 seconds. The intact white and residual red blood cells were then centrifuged for 12 seconds at 13,000 g in a microcentrifuge. The supernatant was removed by gentle aspiration using a low pressure vacuum pump system. A further 450 μl of TE buffer was then added to lyse the remaining red blood cells and the white blood cells collected by centrifugation as before. If any redness remained in the pellet, this process was repeated until the pellet was white. After removal of the last drop of supernatant from the pelleted white blood cells, 100 μl of K buffer containing proteinase K was added and the mixture incubated at 55° C. for 2 hours. The mixture was then heated to 95–100° C. for 8 minutes and the DNA lysates stored at −20° C. until needed.

| Reagents. | |
|---|---|
| TE buffer: | 10 mM TRIS-HCl pH 8.0 |
| | 1 mM EDTA |
| K buffer: | 50 mM KCl |
| | 10 mM TRIS-HCl pH 8.3 |
| | 2.5 mM $MgCl_2$ |
| | 0.5% Tween 20 |

Prior to use for lysates, 10 μl of 20 mg/ml proteinase X (Molecular Probes Inc.) per 1.0 ml of K buffer was added.

(ii) PCR

Reactions were set up as follows in thin walled 0.25 ml tubes (Perkin Elmer):

4.0 μl 5 μM CRC Forward primer;

4.0 μl 5 μM CRC Reverse primer;

4.0 μl 5 μM KIT1-REV primer;

4.0 μl 5 μM KIT1-FOR primer;

4.0 μl 2 mM dNTPs (Pharmacia);

4.0 μl 35 mM $MgCl_2$.

A wax bead (PCR Gem 50, Perkin Elmer) was added and the tube placed in a Perkin Elmer 9600 thermal cycler. The tube was then raised to 80° C. for 15 seconds followed by cooling to 4° C. A second set of reagents was then added to each tube as below:

4.0 μl 10x buffer;

9.6 μl sterile deionised water;

0.4 μl (0.5 units) Amplitaq DNA polymerase (Perkin Elmer);

2 μl DNA lysate.

Reaction tubes were then placed on a Perkin Elmer 9600 thermal cycler preheated to 94° C. and PCR carried out according to the regime indicated below:

94° C. for 4 minutes;

20 cycles of 94° C. for 30 secs, 62° C. for 30 secs and 72° C. for 30 secs;

0° C. until required.

The number of cycles may vary depending upon the tissue used as the DNA source.

KIT primers (SEQ ID NO:1)

Forward GAATATTGTTGCTATGGTGATCTCC KIT1-FOR (SEQ ID NO:2)

Reverse CCGCTTCTGCGTGATCTTCCTG KIT1-REV

CRC primers (SEQ ID NO:9)

Forward CTGGATGTCCTGTGTTCCCTGT CRC-FORWARD (SEQ ID NO:10)

Reverse AGGTTTGTCTGCAGCAGAAGCTC CRC-REVERSE

The reverse KIT primer and the forward CRC primer are labelled with the ABI fluorescent dye FAM at the 5' end.

(iii) Electrophoresis and Quantitation of DNA Fragments

1 μl of the PCR was mixed with 2.5 μl of deionised formamide, 0.5 μl of GS350 DNA standards, 0.4 μl blue dextran solution, heated at 90° C. for 2 minutes followed by rapid cooling on ice. 3 μl of this mix were then loaded onto an AB1373 DNA sequencer and DNA fragments separated on a 6% polyacrylamide gel in 1×TBE buffer for 2 hours at 700 V, 40 mA, 32 W. The fragments corresponding to the products from the KIT and CRC genes were quantitated using GeneScan software, the peak area for each of the bands being determined.

(iv) Results

The data given in Table 1 represents the results obtained from an experiment in which DNA lysates were produced from each of 23 animals, with two PCR tests being carried out on each lysate. The ratio of KIT peak area to CRC peak area was calculated for each PCR and the average taken of those samples from the same animal.

TABLE 1

| Animal | Genotype | KIT/CRC peak area ratio |
|---|---|---|
| 1 | II | 3.25 |
| 2 | Ii | 2.45 |
| 3 | II | 2.94 |
| 4 | ii | 1.16 |
| 5 | ii | 1.34 |
| 6 | ii | 1.20 |
| 7 | Ii | 2.18 |
| 8 | Ii | 2.19 |
| 9 | II | 2.88 |
| 10 | ii | 1.30 |
| 11 | Ii | 1.84 |
| 12 | II | 2.84 |
| 13 | ii | 1.50 |
| 14 | ii | 1.30 |
| 15 | Ii | 2.07 |
| 16 | ii | 1.31 |

TABLE 1-continued

| Animal | Genotype | KIT/CRC peak area ratio |
|---|---|---|
| 17 | ii | 1.14 |
| 18 | Ii | 2.02 |
| 19 | Ii | 1.87 |
| 20 | Ii | 2.00 |
| 21 | ii | 0.99 |
| 22 | ii | 1.15 |
| 23 | II | 2.80 |

The upper and lower limits for the ratio values from animals of the different genotypes II, Ii and ii in this experiment are as below:

| Genotype | Upper Limit | Lower Limit |
|---|---|---|
| I/I | 3.25 | 2.80 |
| I/i | 2.45 | 1.84 |
| i/i | 1.50 | 0.99 |

These results illustrate differentiation of the genotypes using this test.

EXAMPLE 2

The second test utilises unique sequences of DNA that are present at one end of the duplication (or both ends if the duplicated region is reversed relative to the rest of the gene or if the duplicated region does not occur in direct tandem with the non-duplicated region). Oligonucleotide primers for use in PCR are designed such that at the annealing temperatures used in the PCR process, they will anneal only to the junction regions at the end of the duplicated region. A PCR is then carried out using two pairs of oligonucleotides. One pair consists of the aforementioned primer spanning the junction region and a second primer a suitable distance away which allows amplification to occur only from I allele containing duplication. The second pair of primers allow amplification of a sequence present only as a single copy in the haploid genome. The product of this reaction, carried out in the same tube, functions as an internal standard as in the previous test. The ratio of product from the reaction specific to the junction region is measured relative to that from the single copy control sequence.

In this test there is a larger difference between the predicted ratios of the products from the different genotypes. The relative levels of product and their ratios are illustrated below:

| Genotype | Junction Product | Control Product | Ratio |
|---|---|---|---|
| II | 2 | 2 | 1:1 |
| Ii | 1 | 2 | 1:2 |
| ii | 0 | 2 | 0:2 |

These larger ratios allow greater differentiation between the ranges of results obtained from the different genotypes, reducing risks of miss-scoring animals.

EXAMPLE 3

(i) DNA Preparation

DNA can be prepared as described in EXAMPLE 1

(ii) PCR

Reactions were set up as follows in thin walled 0.25 ml tubes (Perkin Elmer):

2.0 μl 5 mM KITDEL2-FOR primer;

2.0 μl 5 mM KITDEL2-REV primer;

1.0 μl 2 mM dNTPs (Pharmacia);

1.2 μl 25 mM MgCl2

2.0 μl 10× buffer (without MgCl2)

0.1 μl (0.5 units) AmpliTaq DNA polymerase (Perkin Elmer);

2.0 μl DNA lysate;

9.7 μl sterile deionised water.

Reaction tubes were then placed on a Perkin Elmer 9600 thermal cycler and PCR carried out according to the regime indicated below:

95° C. for 1 minute;

3 cycles of 95° C. for 15 secs, 50° C. for 20 secs and 72° C. for 40 secs;

27 cycles of 94° C. for 15 secs, 50° C. for 20 secs and 72° C. for 50 secs;

72° C. for 5 minutes;

4° C. until required.

The number of cycles may vary depending upon the tissue used as the DNA source.

KIT primers

Forward GAAAGTGA(C/T)GTCTGGTCCTAT(C/G)GGAT KITDEL2-FOR (SEQ ID NO:15)

Reverse AGCCTTCCTTGATCATCTTGTAG KITDEL2-REV (SEQ ID NO:16)

(iii) Electrophoresis

1 μl of the PCR product was mixed with 3 μl loading buffer (95% deionised formamide, 10 mM NaOH, 20 mM EDTA, 0.05% bromophenolblue, 0.05% Xylene-cyanol), heated to 95° C. for 3 minutes followed by rapid cooling on ice. The sample was then loaded on an 8% native polyacrylamide gel (Protogel, 37.5:1 Acrylamide:bisacrylamide, National Diagnostics, Atlanta) in 1× TBE buffer (89 mM Tris, 89 mM boric acid, 2 mM EDTA.Na2). The DNA fragments were separated by electrophoresis for 4.5 hours at 6 W with a constant temperature of 20° C. and 0.6× TBE as running buffer in a vertical slab unit (SE600 Hoefer Scientific Instruments, San Francisco).

(iv) Visualisation of DNA fragments by silver staining

After electrophoresis the gel was incubated, with gentle agitation, in the fix solution for 20 minutes or until the tracking dyes were no longer visible. The gel was rinsed three times (2 minutes each with agitation) in deionised water. The gel was then incubated in the staining solution for 40 minutes, with gentle agitation, followed by a brief wash (5–10 seconds) in deionised water and direct transfer to the developing solution. The gel was incubated in the developing solution until bands were clearly visible and then the development was terminated by adding an equal volume of fix solution. Finally, the gel was rinsed for 2 minutes in deionised water.

| Reagents. | |
|---|---|
| Fix solution: | 10% glacial acetic acid in deionised water |
| Staining solution: | 2 g silver nitrate (AgNO3) 3 ml 37% formaldehyde 2 liters deionised water |
| Developing solution: | 60 g sodium carbonate (Na2CO3) dissolved in 2 liters deionised water. Immediately before use add 3 ml 37% formaldehyde and 400 ml sodium thiosulfate (10 mg/ml). The solution should be at a temperature of 10–12° C. when used. |

(v) Results

This SSCP analysis reveals an informative polymorphism so far only found in animals with the dominant white phenotype (FIG. 1). In lanes 1 to 8 the analysis was carried out on DNA from Swedish Landrace pigs carrying the dominant white colour and in lanes 9 and 10 DNA was from wild pigs of wild type colour. The polymorphic bands are indicated. The polymorphism is characterised by two unique fragments only present in animals carrying a duplicated KIT gene of allele type I. The fragments represent haeteroduplexes of DNA strands from PCR products of unequal length representing the duplicated and non-duplicated copy of the KIT gene. The results of a screening test with this marker using 40 unrelated animals representing five breeds and 190 F2 animals from a Large White/Wild pig intercross are presented in Table 2.

The results show that this particular polymorphism is very closely associated with the presence of the KIT duplication. It is not completely associated with the duplication as some white animals did not show the heteroduplex pattern. The polymorphism is therefore an example of a closely linked genetic marker which by itself or in combination with other linked markers can be used to differentiate genotypes as regards the dominant white coat colour.

TABLE 2

| | | | HETERODUPLEX | |
|---|---|---|---|---|
| BREED | COLOUR | NO. OF ANIMALS | PRESENT | NOT PRESENT |
| SWEDISH LANDRACE | WHITE | 10 | 10 | 0 |
| SWEDISH LARGE WHITE | WHITE | 8 | 8 | 0 |
| SWEDISH HAMPSHIRE | COLOURED | 10 | 0 | 10 |
| SWEDISH DUROC | COLOURED | 10 | 0 | 10 |
| WILD PIG | COLOURED | 2 | 0 | 2 |
| LARGE WHITE/ WILD PIG INTERCROSS | WHITE PATCH COLOURED | 131 9 50 | 106 0 0 | 25 9 50 |

EXAMPLE 4 i) DNA extraction

DNA was prepared as in example 1.

ii) PCR

Reactions were set up in 0.25 ml thin walled reaction tubes (Perkin Elmer) as follows:

| | | |
|---|---|---|
| 0.5 | ml | 5 µM KITDEL1-FOR primer |
| 0.5 | ml | 5 µM KITDEL1-REV primer |
| 1.0 | ml | 2 mM dNTPs (Pharmacia) |
| 1.0 | ml | 15 mM MgCl$_2$ |
| 1.0 | ml | 10 X buffer |
| 4.9 | ml | Sterile distilled water |
| 0.1 | ml | AmpliTaq DNA polymerage |
| 1.0 | ml | DNA luysate |

Reaction tubes were then placed in a Perkin Elmer 9600 thermal cycler and PCR carried out according to the regime 94° C. for 4 minutes;

21 cycles of 94° C. for 30 sec, 60° C. for 30 sec, and 72° C. for 30 sec;

72° C. for 4 min;

4° C. until required.

The number of cycles used may vary depending on the tissue used as the source of the DNA.

Primers (SEQ ID NO:13)

forward TGTGGGAGCTCTTCTCTTTAGG KITDEL1-FOR (SEQ ID NO:14)

reverse CCAGCAGGACAATGGGAACATCT KITDEL1-REV

The reverse primer was labeled with the ABI fluorescent dye FAM at the 5' end.

iii) Electrophoresis and quantitation of DNA fragments 1 µl of the PCR was mixed with 1.5 µl of deionised formamide, 0.25 µl of GS350 DNA standards, 0.25 µl loading buffer (50 mg/ml blue dextran, 25 mM EDTA) and heated at 90° C. for two minutes followed by rapid cooling on ice. 1.75 µl of this was then loaded onto an ABI 377DNA sequencer and DNA fragments separated on a 4.12% polyacrylamide gel in 1× TBE buffer for two hours at 3000 V, 60 mA, 200 W and 48° C. The 97 bp and 93 pb fragments corresponding to the products from the KIT gene template lacking the deletion and containing the deletion respectively were quantitated using GeneScan software, the peak area for each of the bands being determined.

Results

The data given in the table below represents the results obtained from an experiment in which DNA lysates were produced from each of 20 animals of known genotypes with one PCR test being carried out on each lysate. The ratio of the peak area of the product from the DNA template not containing the four base pair deletion to that containing the deletion was calculated.

TABLE 3

| ANIMAL | GENOTYPE | Non del/del peak area ratio |
|---|---|---|
| 1 | II | 1.347 |
| 2 | II | 1.21 |
| 3 | II | 1.33 |
| 4 | II | 2.267 |
| 5 | II | 0.444 |
| 6 | II | 0.713 |
| 7 | II | 8.387 |
| 8 | II | 0.994 |
| 9 | II | 1.673 |
| 10 | II | 1.056 |
| 11 | Ii | 1.751 |
| 12 | Ii | 1.73 |
| 13 | Ii | 1.83 |
| 14 | Ii | 0.631 |
| 15 | Ii | 1.975 |
| 16 | Ii | 2.147 |
| 17 | Ii | 1.901 |
| 18 | Ii | 1.749 |
| 19 | Ii | 2.103 |
| 20 | Ii | 2.026 |

For this small sample the value of 1.5 which is midway between the predicted ratio values for each genotype (expected ratio=2 for Ii and 1 for II) might be used as the dividing line for scoring the animals to either genotype. It can be determined from the table that 7/10 II and 9/10 Ii are identified as the correct genotype.

This invention includes methods based on specific binding between assay components and a potion of the KIT gene or a protein sequence expressed therefrom. Assay components include nucleic acids that specifically bind nucleic acids of the KIT gene or specifically bind nucleic acids of the KIT gene comprising deletions described herein as well as antibodies which specifically bind to the gene product of the KIT gene or antibodies which specifically bind to the gene product of the KIT gene comprising deletions described herein.

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in veterinary medicine, animal husbandry, immunodiagnostics, nucleic acid analysis and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference. In particular, the following documents are incorporated by reference to the extent that they facilitate making or using the invention:

Johansson et al., Genomics 14:965–969 (1992)
Chabot et al., Nature 335:88–89 (1988)
Geissler et al., Cell 55:185–192 (1988)
Nocka et al., EMBO Journal 9:1805–1813 (1990)
Artursson et al., Journal of Interferon Research 12: 153–160 (1992)
Kato et al., Journal of Molecular Endocrinology 7:27–34 (1991)
Ezashi et al., Journal of Molecular Endocrinology 5:137–146 (1990)
Ellegren et al., Genomics 16:431–439 (1993)
Coppieters et al., Animal Genetics 24:163–170 (1993)
Rhorer et al., Genetics, 136:231–245 (1994)
Gokkel et al., Oncogene 7, 1423–1429 (1992)
Giebel et al., Oncogene 7, 2207–2217 (1992)
Besmer et al., Nature 320:415–421 (1986)

We claim:

1. A screening method to determine the presence or absence of duplication of all or part of a KIT gene to distinguish coat color genotype of a pig which comprises the steps of:
   a) obtaining a sample of pig nucleic acid; and
   b) analyzing the pig nucleic acid to determine whether duplication of all or part of the KIT gene is present, wherein the presence of said duplication indicates the genotype for absence of coat color in the pig and the absence of said duplication indicates the genotype for colored coat in the pig.

2. The method of claim 1 wherein the pig nucleic acid is genomic DNA.

3. The method of claim 2 further comprising the step of determining whether any duplication present is due to the presence of an I allele, and $I^P$ allele, or both an I allele and an $I^P$ allele.

4. The method of claim 3 wherein said analyzing step includes generating KIT gene amplification products by amplifications of at least a part of the KIT gene by means of one or more cycles of polymerase chain reaction (PCR) using a pair of suitable primers.

5. The method of claim 4 wherein the amplification products are quantified.

6. The method of claim 4 wherein the pair of primers is selected from the group of primer pairs consisting of:
   a) GAATATTGTTGCTATGGTGATCTCC (SEQ ID NO:1) and CCGCTTCTGCGTGATCTTCCTG (SEQ ID NO:2);
   b) GG(C/T)AATCACATGAATATTGTGAA (SEQ ID NO:3) and TCACCATAGCAACAATATTCTGT (SEQ ID NO:4);
   c) TC(A/G)TACATAGAAAGAGA(C/T)GTGACTC (SEQ ID NO:5) and CCTTT(A/G)ACCAC(A/G)TAATT(A/C)GAATC (SEQ ID NO:6); and
   d) GTGATG(A/G)T(G/T)CT(C/G)ACCTACAAATA (SEQ ID NO:7) and GTCTATGTAAACATAAT-TGTTTCC (SEQ ID NO:8).

7. The method of claim 4 wherein the pair of primers hybridizes to a sequence unique to the I allele located at the boundary of the KIT gene and the duplicated region to thereby determine the presence of the I allele.

8. The method of claim 5 further comprising the step of comparing the quantity of KIT gene amplification products with the quantity of amplification products of a standard.

9. The method of claim 8 wherein the standard is generated by amplification of a reference nucleotide sequence by means of one or more cycles of polymerase chain reaction using a second pair of suitable primers to generate reference sequence amplification products.

10. The method of claim 9 wherein the reference sequence amplification products are quantified.

11. The method of claim 10 wherein the reference nucleotide sequence is at least a part of the sequence of the muscle calcium release channel gene.

12. The method of claim 11 wherein a set of primers comprising the sequences of CTGGATGTCCTGTGTTC-CCTGT (SEQ ID NO:9) and AGGTTTGTCTGCAGCA-GAAGCTC (SEQ ID NO:10) is used for the standard polymerase chain reaction.

13. The method of claim 9 wherein the reference nucleotide sequence is at least a part of the sequence of the porcine interferon-βgene.

14. The method of claim 13 wherein a set of primers comprising the sequences of GATGAACTTTGAGGTC-CCTGAGGAG (SEQ ID NO:11) and TTTCTTCT-GAGAATGCCGAAGATCTG (SEQ ID NO:12) is used for the standard polymerase chain reaction.

15. The method of claim 9 wherein amplification of the reference nucleotide sequence to generate the standard is performed simultaneously with the amplification of at least part of the KIT gene.

16. The method of claim 9 wherein the ratio of the quantity of KIT gene amplification products to the quantity of reference sequence amplification products is determined.

17. The method of claim 13, wherein the presence or absence of the I allele is determined by identifying a deletion in at least one duplication of the KIT gene, wherein the presence of a deletion in at least one duplication of the KIT gene is indicative of the presence of the I allele.

18. The method of claim 17 wherein the ratio of the quantity of duplications of the KIT gene which do not contain a deletion to the quantity of duplications of the KIT gene which do contain a deletion is determined to identify the presence or absence of the $I^P$ allele.

19. A kit for determining the coat color genotype of a pig, wherein said kit is adapted to be used with a sample of pig nucleic acid and said kit comprises (a) one or more reagents for carrying out PCR, said regents being capable of indicating the presence of duplication of all or part of the KIT sequence and (b) at least one pair of primers.

20. The kit of claim 19, wherein the pig nucleic acid is pig genomic DNA.

21. The kit of claim 20 wherein the at least one pair of primers is selected from the group consisting of:
   a) GAATATTGTTGCTATGGTGATCTCC (SEQ ID NO:1) and CCGCTTCTGCGTGATCTTCCTG (SEQ ID NO:2);
   b) GG(C/T)AATCACATGAATATTGTGAA (SEQ ID NO:3) and TCACCATAGCAACAATATTCTGT (SEQ ID NO:4);
   c) TC(A/G)TACATAGAAAGAGA(C/T)GTGACTC (SEQ ID NO:5) and CCTTT(A/G)ACCAC(A/G)TAATT(A/C)GAATC (SEQ ID NO:6); and
   d) GTGATG(A/G)T(G/T)CT(C/G)ACCTACAAATA (SEQ ID NO:7) and GTCTATGTAAACATAATTGTTTCC (SEQ ID NO:8).

22. The kit of claim 19 wherein the pair of primers hybridizes to a unique region located at the boundary of the KIT gene and the duplicated region.

23. The kit of claim 19 further comprising a second pair of primers allowing amplification of at least a part of another nucleotide sequence by means of one or more cycles of polymerase chain reaction.

24. The kit of claim 23 wherein the second pair of primers hybridizes to at least a part of the sequence of the muscle calcium release channel (CRC) gene.

25. The kit of claim 24 wherein the second pair of primers comprises the sequences of CTGGATGTCCTGTGTTCCTGT (SEQ ID NO:9) and AGGTTTGTCTGCAGCAGAAGCTC (SEQ ID NO:10).

26. The kit of claim 23 wherein the second pair of primers hybridizes to at least a part of the sequence of the porcine interferon-β gene.

27. The kit of claim 26 wherein the second pair of primers comprises the sequences of GATGAACTTTGAGGTCCCTGAGGAG (SEQ ID NO:11) and TTTCTTCTGAGAATGCCGAAGATCTG (SEQ ID NO:12).

28. A screening method to identify the presence or absence of a deletion in a KIT gene to characterize the coat color genotype of a pig comprising the steps of:
   a) obtaining a sample of pig nucleic acid; and
   b) analyzing the nucleic acid to identify the presence or absence of a deletion in the KIT gene, wherein the presence of a deletion in the KIT gene indicates the genotype for absence of coat color and the absence of a deletion indicates the genotype for a colored coat in the pig.

29. The method of claim 28 wherein the pig nucleic acid is genomic DNA.

30. The method of claim 28 wherein said analyzing step comprises the amplification of at least a part of the KIT gene by means of one or more cycles of PCR using at least one pair suitable primers.

31. The method of claim 30 wherein the at least one pair of primers is selected from the group consisting of:
   a) TGTGGGAGCTCTTCTCTTTAGG (SEQ ID NO:13) and CCAGCAGGACAATGGGAACATCT (SEQ ID NO:14) and
   b) GAAAGTGA(C/T)GTCTGGTCCTAT(C/G)GGAT (SEQ ID NO:15) and AGCCTTCCTTGATCATCTTGTAG (SEQ ID NO:16).

32. The method of claim 30 wherein the presence of a deletion in the KIT gene is indicative of the presence of the I allele.

33. A kit for use in determining the coat color genotype of a pig, wherein said kit is adapted to be used with a sample of pig nucleic acid and said kit comprises (a) one or more reagents for performing polymerase chain reactions, said reagents being capable of indicating the presence or absence of a deletion in the KIT sequence and (b) at least one pair of primers.

34. The kit of claim 33, wherein the pig nucleic acid is pig genomic DNA.

35. The kit of claim 34 wherein the at least one pair of primers is selected from the group consisting of:
   a) TGTGGGAGCTCTTCTCTTTAGG (SEQ ID NO:13) and CCAGCAGGACAATGGGAACATCT (SEQ ID NO:14); and
   b) GAAAGTGA(C/T)GTCTGGTCCTAT(C/G)GGAT (SEQ ID NO:15) and AGCCTTCCTTGATCATCTTGTAG (SEQ ID NO:16).

36. The method of claim 5 wherein the pair of primers is selected from the group of primer pairs consisting of:
   c) GAATATTGTTGCTATGGTGATCTCC (SEQ ID NO:1) and CCGCTTCTGCGTGATCTTCCTG (SEQ ID NO:2);
   b) GG(C/T)AATCACATGAATATTGTGAA (SEQ ID NO:3) and TCACCATAGCAACAATATTCTGT (SEQ ID NO:4);
   c) TC(A/G)TACATAGAAAGAGA(C/T)GTGACTC (SEQ ID NO:5) and CCTTT(A/G)ACCAC(A/G)TAATT(A/C)GAATC (SEQ ID NO:6); and
   d) GTGATG(A/G)T(G/T)CT(C/G)ACCTACAAATA (SEQ ID NO:7) and GTCTATGTAAACATAATTGTTTCC (SEQ ID NO:8).

* * * * *